US00PP25109P3

(12) United States Plant Patent
Roberts

(10) Patent No.: US PP25,109 P3
(45) Date of Patent: Nov. 25, 2014

(54) MINT PLANT 'HOODOO MINT'

(50) Latin Name: ***Mentha* sp.**
Varietal Denomination: HooDoo Mint

(71) Applicant: Essex Laboratories, Inc., Napavine, WA (US)

(72) Inventor: Donald D. Roberts, Independence, OR (US)

(73) Assignee: Essex Laboratories, Inc., Napavine, WA (US)

( * ) Notice: Subject to any disclaimer, the term of this patent is extended or adjusted under 35 U.S.C. 154(b) by 0 days.

(21) Appl. No.: 13/986,042

(22) Filed: Mar. 25, 2013

(65) Prior Publication Data

US 2014/0289918 P1 Sep. 25, 2014

(51) Int. Cl.
*A01H 5/00* (2006.01)

(52) U.S. Cl.
USPC ..... Plt./259

(58) Field of Classification Search
USPC ..... Plt./259
See application file for complete search history.

(56) References Cited

U.S. PATENT DOCUMENTS

PP11,788 P2 * 2/2001 Roberts ..... Plt./259
PP13,720 P2 4/2003 Roberts

OTHER PUBLICATIONS

Gobert, V., "Hybridization in the section *Mentha* (*Lamiaceae*) inferred from AFLP markers," Am. J. Bot, Dec. 2002, 89 (12). pp. 2017-2023.

Rohloff, Jens, et al., Effect of Harvest Time and Drying Method on Biomass Production, Essential Oil Yield, and Quality of Peppermint (*Mentha piperita* L.); J. Agric. Food Chem., 2005, 53 (10), pp. 4143-4148.

Dung, Jeremiah K.S., et al. Evaluation of Verticillium Wilt Resistance in *Mentha arvensis* and *M. longifolia* Genotypes, Plant Disease, Oct. 2010, vol. 94, pp. 1255-1260.

* cited by examiner

*Primary Examiner* — June Hwu
*Assistant Examiner* — Keith Robinson
(74) *Attorney, Agent, or Firm* — Marger Johnson & McCollom, PC

(57) ABSTRACT

Mint selection 09-6-2, denominated 'Hoodoo Mint', is a new *Mentha* sp. cultivar that produces an essential oil different in composition, produces more oil on a dry weight basis and has an upright plant type and resistance to mint rust (*Puccinia menthae*) and mint wilt (*Verticillium dahlia*).

3 Drawing Sheets

Figure 1:
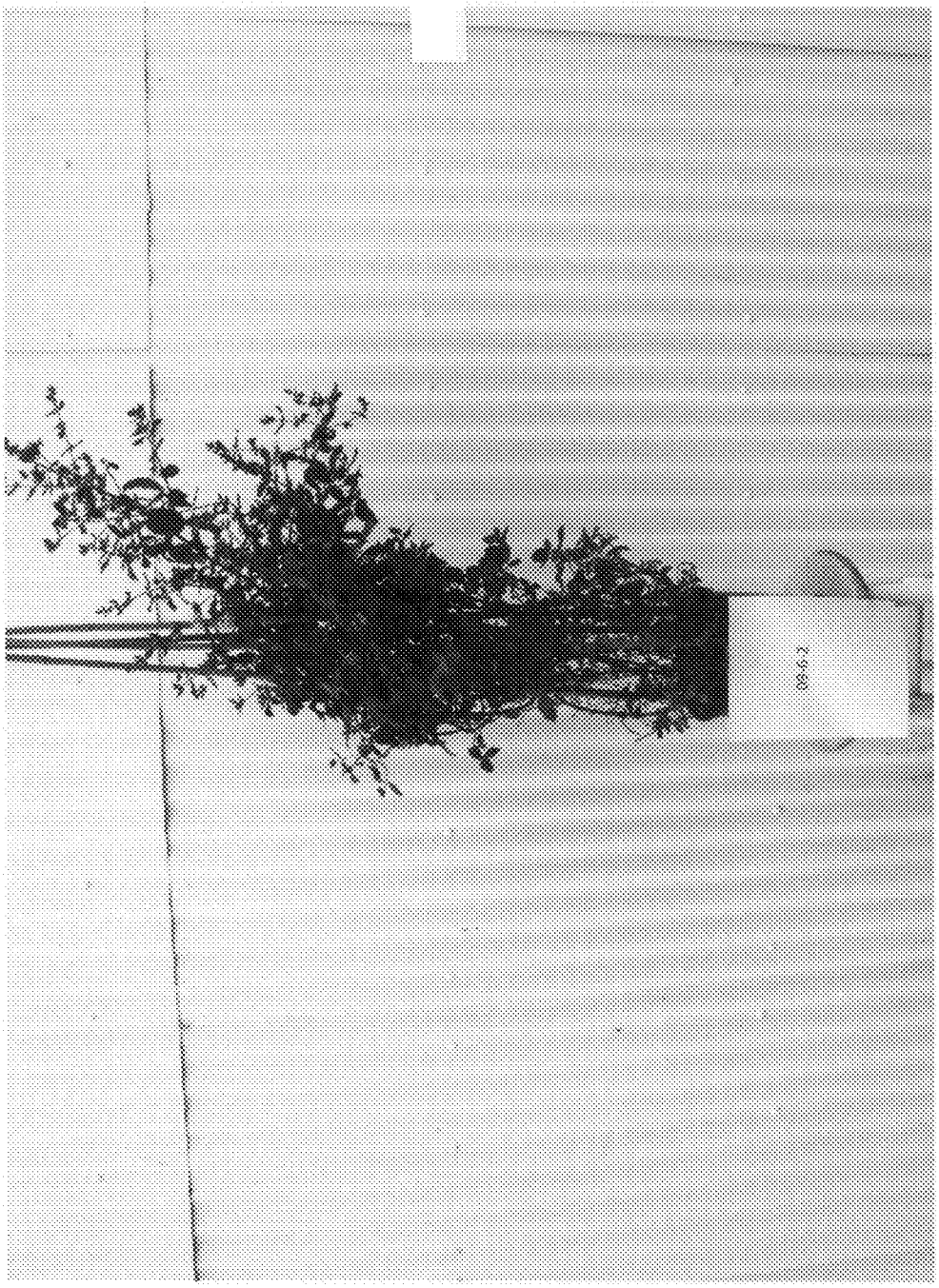

Latin name of the genus and species: *Mentha* sp.
Variety denomination: 'HOODOO MINT'.

TYPE OF PLANT AND NAME OF VARIETY

The present invention relates to a new and distinct variety of peppermint plant developed from a parent of the species *M. arvensis*. The new variety will be identified as 'HooDoo Mint.'

BACKGROUND OF INVENTION

This new mint was developed in a mint breeding program in which the primary objective was to develop a Mitcham type peppermint variety having a specific oil composition, acceptable yield and resistant to mint diseases. The new variety is more resistant to mint rust (air-borne fungus *Puccinia menthae*) and mint wilt (*Verticillium dahliae*). This plant was selected from a population of mint seedlings in research plots on land near Monmouth, Oreg. and initially identified as 09-6-2.

DISCOVERY AND ASEXUAL REPRODUCTION

Selection 09-6-2 originated as a seedling from an open pollinated *Mentha arvensis* var. *piperascens* female parent, 06-Blanco-9. Parent line 06-Blanco-9 is a seedling from the Brazilian commercial variety 'Blanco' and was included with other *M. arvensis* and male fertile *M. piperita* plants in a polycross breeding program. Diploid *M. piperita* is sterile and only becomes fertile in the polyploidy state. The parent plants in the polycross breeding system were composed of selected fertile male and female genotypes based on certain desirable characteristics.

Selection 09-6-2 is asexually propagated to maintain the cultivar's genetic integrity and as a means of increasing the selection for commercial planting. Asexual propagation, by tip cuttings or stolon sections, is a common practice in commercial mint cultivation and serves as a means of propagating the normally sterile mint plant. Under the inventor's direction, Premier Botanicals has conducted asexual propagation of 09-6-2 for greenhouse and field planting since 2009 and the genotype comes true to form with each generation.

SUMMARY OF THE INVENTION

Mint selection 09-6-2 denominated 'HooDoo Mint' is a new *Mentha* sp . cultivar that produces an essential oil different in composition than commercially grown mint varieties. The essential oil is similar to standard mint oil in components composition but differs in the typical ratio of components. Organoleptically it differs from typical *Mentha piperita*

('Black Mitcham') peppermint oil. It is more resistant to mint rust and mint wilt than current commercially grown *Mentha arvensis* varieties.

BRIEF DESCRIPTION OF THE PHOTOGRAPHS

The accompanying color photographs show typical, greenhouse and field grown vegetative growth of 09-6-2 and depicts the color as nearly as reasonably possible.

Photograph 1 illustrates the flowering pattern and multiple flowering shoots of my new mint plant in accordance with the present invention.

Photograph 2 illustrates the shape of flower development in a terminal flowering spike of 09-6-2.

Photograph 3 illustrates the bushy, upright growth pattern of 09-6-2 under field conditions.

DESCRIPTION OF PLANT

My new mint plant improves upon and is distinct from other mint plants in several characteristics, including but not limited to, the following:

1. The ability to produce an essential oil different in composition than typical commercial *M. arvensis* or *M. piperita* varieties, but with similar components as 'Black Mitcham' peppermint (*M. piperita*);
2. The ability to produce more oil on a dry weight basis than currently grown mint varieties;
3. A more upright plant type but with a branching pattern similar to its parent;
4. A level of resistance to mint rust equal to or greater than that of its *M. arvensis* female parent;

The essential oil extracted from 09-6-2 has a composition of components that is different than that of commercial oil produced by 'Black Mitcham' peppermint (*M. piperita*) and *M. arvensis* as illustrated in Table 1. The concentration of menthone in oil of 09-6-2 is greater than that of *M. arvensis* and *M. piperita*. There is a higher concentration of menthofuran in the oil of 09-6-2 than is present in the oil of its parent *M. arvensis* (06-Blanco-9) and lower than that in the oil of commercial peppermint (*M. piperita*). The presence of 1-8-Cineole in 09-6-2 is lower than that in the oil of commercial *M. piperita*. The menthol concentration is lower in 09-6-2 than that in oil of *M. arvensis*. Organoleptically the oil of 09-6-2 is different than that of 'Black Mitcham' and *M. arvensis*, reflecting the difference in oil component ratios. The fragrance of the leaf is a mild peppermint note and void of the strong menthol notes of commercial mints.

One of the primary selection pressures in the breeding program is for disease resistance, primarily for mint rust (*Puccinia menthae*) and mint wilt (*Verticillium dahliae*). No symptoms of either disease were observed in 09-6-2 in multiple plant plots over a three year period. 'Blanco' and 'Black Mitcham' mint varieties served as control plants in the evaluation.

TABLE 1

A Comparison of 09-6-2 Essential Oil collected from test plots near Monmouth, Oregon to that of its *M. arvensis* parent, Commercial *M. arvensis*, and Commercial *M. piperita* Oils. 1/

| Essential Oil Components | 06-Blanco-9 *Mentha arvensis* Parent seedling 2/ | 09-6-2 Seedling 2/ | 'Shivalik' Commercial *M. arvensis* | 'Black Mitcham' Commercial *M. piperita* |
|---|---|---|---|---|
| 1-Limonene | 3.0 | 3.7 | 3.0 | 1.7 |
| 1,8-Cineole | <1.0 | <1.0 | <1.0 | 4.9 |
| 1-Menthone | 15.7 | 31.9 | 7.3 | 19.4 |
| Menthofuran | 0.0 | 2.3 | 0.0 | 4.2 |
| Isomenthone | 3.5 | 1.2 | 3.6 | 3.1 |
| 1-Menthyl Acetate | 3.7 | 5.5 | 2.9 | 5.3 |
| 1-Menthol | 64.3 | 39.1 | 73.9 | 44.6 |
| Pulegone | <1.0 | <1.0 | 0.0 | 2.1 |

The numbers listed in the above table are percentages based upon the analysis of the respective mint oils by gas chromatography. The percentages are determined by calculation of the relative peak areas.
1/Commercial essential oils of *M. arvensis* and *M. piperita* were what is typically produced by mint growers.
2/The essential oil of *M. arvensis* parent seedling 06-Blanco-9 and 09-6-2 were collected from plants growing in test plots in 2010.

TAXONOMIC DESCRIPTION OF 09-6-2

This new plant, under greenhouse and field growing conditions, has an upright growth habit with lateral branches at each node of the main stems (Photographs 1 and 3). The plant has secondary and tertiary branching that occurs up to flowering. The height of 09-6-2 at maturity is equal to or greater than 'Black Mitcham,' ranging between 1 to 1.3 m, growing under similar conditions and will vary based on fertilizer, soil quality, and water application, amongst other known factors that affect growth patterns. The plant width also varies, depending on management, but when measured on growth from a main stem, the width ranges from 0.35 to 0.46 m at the eleventh node. When 09-6-2 is mature and ready for harvest, the main stem at mid-plant (approximately between the eleventh and twelfth node) is 4.0-6.0 mm in width. The secondary and tertiary branch stems are 2.0-3.1 mm and 1-2 mm in width, respectively.

Mature leaves at the bottom of the plant are ovate and leaves on secondary branch stems are ovate to lanceolate. Leaves on upper mature plants, both main and secondary stems are more lanceolate. The upper leaf surface is glabrose and lower surface is sub-glabrose with oil glands distributed across the surface. Mid-main stem leaf size at flowering is 28-32 mm in width and 56-59 mm in length. Leaf size on secondary branches at flowering is 16-20 mm in width and 28-32 mm in length. Leaf petioles on the main stem leaves are 9-12 mm in length while petioles on secondary branch stem leaves are 4-6 mm in length. Leaves tend to be more irregular dentate than 'Black Mitcham' peppermint leaves. The main stem leaves are serrate and have from 19-22 teeth on each side while the secondary branch leaves have 15-18 teeth on each side. The leaf is green in color, ranging from Fifth Edition Royal Horticultural Society Colour Chart 147A to 147B in the Fan 3 yellow green group classification. The leaf has 6-8 lateral veins, more or less in parallel off the main vein that runs from the petiole to the tip of the leaf. The veins are prominent in all leaves of 09-6-2.

The inflorescence is a conspicuous spike with capitate flowers developing at the nodes of the spike stem (Photograph 2). The cylindrical spikes are indeterminate. The capitate flowers are 15-20 mm in width and 10-15 mm in length. The flowers consist of five petals fused into a two lipped corolla.

The corolla is light violet in color as illustrated in the Fifth Edition Royal Horticultural Society Colour Chart 85D in the Fan 2 Violet Group. The calyx is generally yellow green and is 143B to 143C, Fan 3 Green Group, as illustrated in the Fifth Edition Royal Horticultural Colour Chart index. The gynoecium consists of a single pistil with two lobed stigma that is exserted. The androecium consists of four stamens, each with a distinct filament and anther. Seed from 09-6-2, at maturity are brown (Fifth Edition Royal Horticultural Society Colour Chart 177A, Fan 4 Greyed-Orange Group) to black (Fifth Edition Royal Horticultural Society Colour Chart 203B, Fan 4 Black Group) in color, oval in shape, with a width of 0.5 to 0.6 mm and a length of 0.6 to 0.8 mm.

While the plant that comprises the present invention has been described in connection with a specific embodiment thereof, it will be understood that this application is intended to cover any variation, uses, or adaptation of the invention (particular those induced by cultivation under different environmental conditions) following, in general the principles of the invention and including such departures from the present disclosure as come within known or customary practice in the art to which the invention pertains and as may be applied to the essential features hereinbefore set forth, and as fall within the scope of the invention and the limits of the appended claim.

I claim:

1. A new and distinct variety of peppermint plant, substantially as shown and described, characterized particularly by improving resistance to mint rust and mint wilt, producing a unique essential oil.

* * * * *

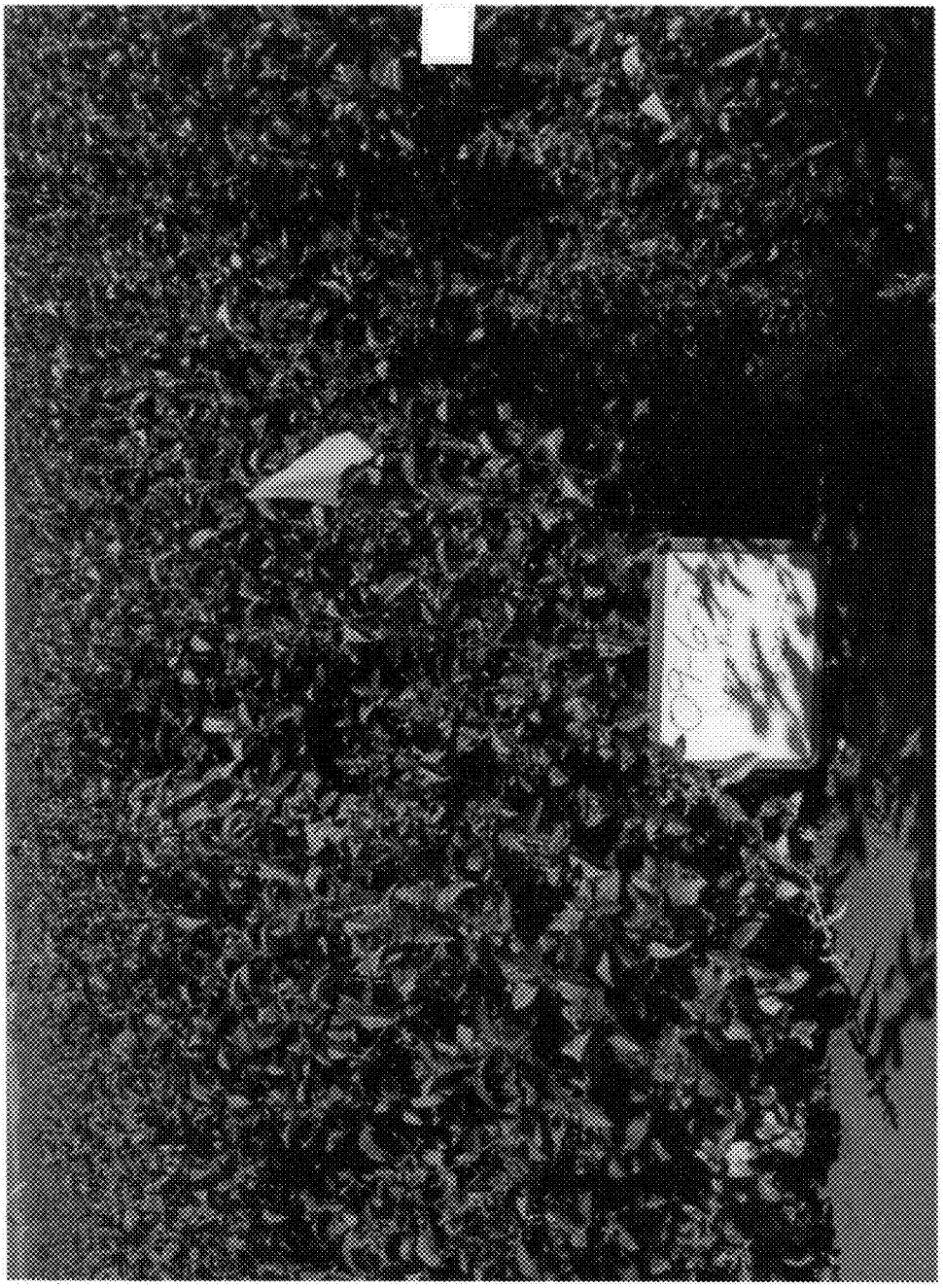

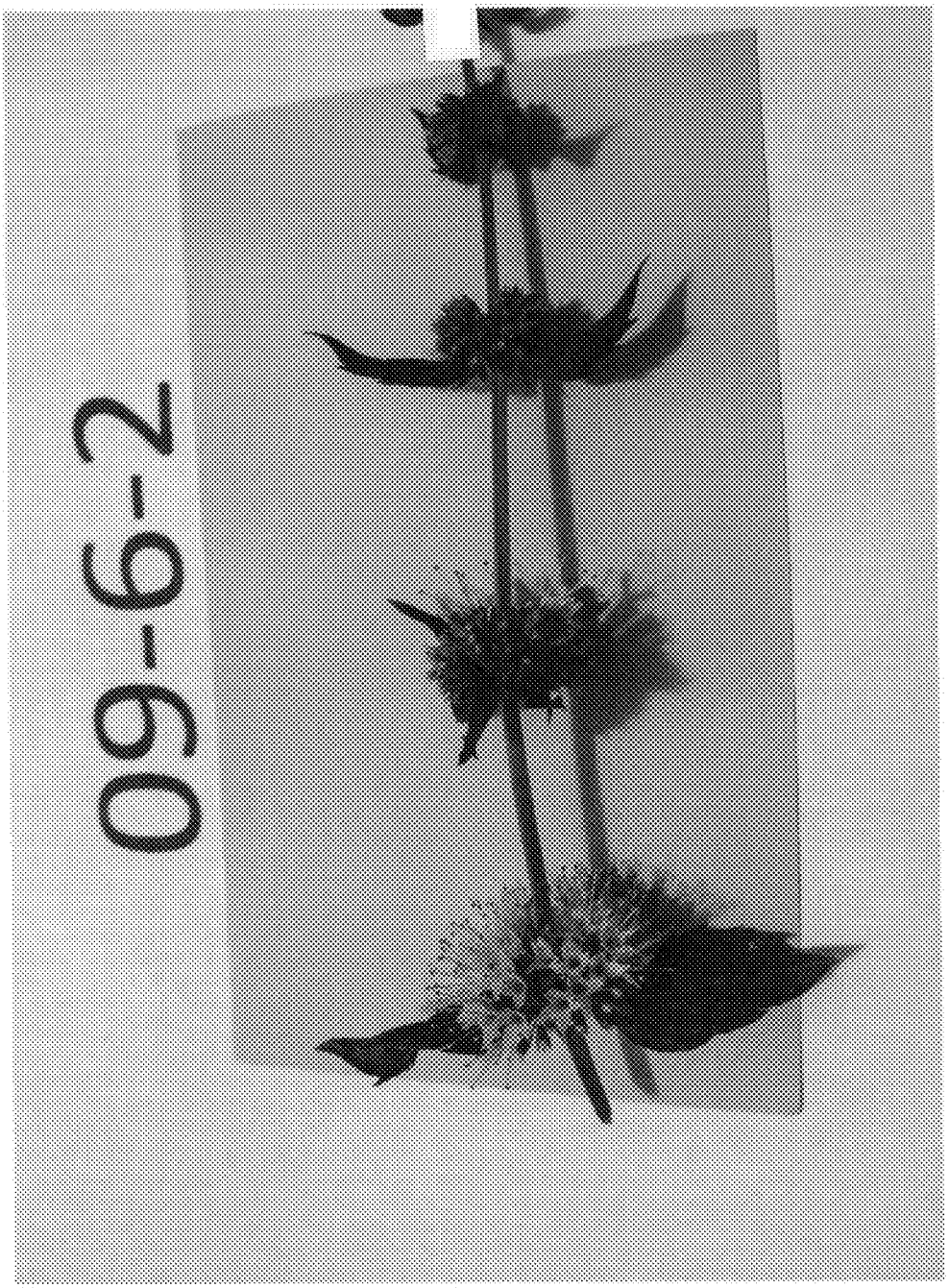
2-9-09